US012281055B2

(12) United States Patent
Green et al.

(10) Patent No.: US 12,281,055 B2
(45) Date of Patent: Apr. 22, 2025

(54) TWO-DIMENSIONAL COORDINATION POLYMERS

(71) Applicant: Arizona Board of Regents on behalf of Arizona State University, Scottsdale, AZ (US)

(72) Inventors: Matthew Green, Phoenix, AZ (US); Sefaattin Tongay, Tempe, AZ (US); Meng Wang, Tempe, AZ (US); Ying Qin, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 352 days.

(21) Appl. No.: 17/841,150

(22) Filed: Jun. 15, 2022

(65) Prior Publication Data

US 2022/0306566 A1    Sep. 29, 2022

Related U.S. Application Data

(62) Division of application No. 16/852,288, filed on Apr. 17, 2020, now Pat. No. 11,390,576.

(60) Provisional application No. 62/836,125, filed on Apr. 19, 2019.

(51) Int. Cl.
*C07C 209/32* (2006.01)
*C08F 4/60* (2006.01)
*C07C 211/58* (2006.01)

(52) U.S. Cl.
CPC ........ *C07C 209/32* (2013.01); *C08F 4/60013* (2013.01); *C07B 2200/13* (2013.01); *C07C 211/58* (2013.01)

(58) Field of Classification Search
CPC . C07C 211/58; C07C 209/32; C08F 4/60013; C07B 2200/13
See application file for complete search history.

(56) References Cited

U.S. PATENT DOCUMENTS

| | | | |
|---|---|---|---|
| 11,111,424 B2 | 9/2021 | Yana Motta et al. | |
| 11,390,576 B2* | 7/2022 | Green | C08F 4/60013 |
| 11,524,316 B2* | 12/2022 | Wang | B05D 1/38 |
| 2016/0248114 A1* | 8/2016 | Huskinson | B29C 48/2528 |
| 2018/0194895 A1 | 7/2018 | Ahn et al. | |
| 2020/0131416 A1 | 4/2020 | Smith | |
| 2020/0247966 A1 | 8/2020 | Wang et al. | |
| 2020/0331843 A1 | 10/2020 | Green et al. | |

FOREIGN PATENT DOCUMENTS

| | | |
|---|---|---|
| CN | 109251321 A | 1/2019 |
| EP | 3184578 A1 | 6/2017 |

OTHER PUBLICATIONS

Berke, K.; Tongay, S.; McCarthy, M. A.; Rinzler, A. G.; Appleton, B. R.; Hebard, A. F., "Current transport across the pentacene/CVD-grown graphene interface for diode applications," J Phys Condens Matter 2012, 24 (25), 255802, 7 pages.

Cai, H.; Chen, B.; Wang, G.; Soignard, E.; Khosravi, A.; Manca, M.; Marie, X.; Chang, S. L. Y.; Urbaszek, B.; Tongay, S., "Synthesis of Highly Anisotropic Semiconducting GaTe Nanomaterials and Emerging Properties Enabled by Epitaxy," Advanced Materials 2017, 29 (8), 1605551-n/a, 7 pages.

Cai, H.; Soignard, E.; Ataca, C.; Chen, B.; Ko, C.; Aoki, T.; Pant, A.; Meng, X.; Yang, S.; Grossman, J.; Ogletree, F. D.; Tongay, S., "Band Engineering by Controlling vdW Epitaxy Growth Mode in 2D Gallium Chalcogenides," Advanced Materials 2016, 28:7375-7382.

CAS Abstract and Indexed Compounds, B. Huskinson et al., US 2016/0248114, 2016, 5 pages.

Chen, B.; Wu, K.; Suslu, A.; Yang, S.; Cai, H., Yano, A.; Soignard, E.; Aoki, T.; March, K.; Shen, Y.; Tongay, S., "Controlling Structural Anisotropy of Anisotropic 2D Layers in Pseudo-1D/2D Material Heterojunctions," Advanced Materials 2017, 29:1701201, 8 pages.

Colson, J. W.; Dichtel, W. R., "Rationally synthesized two-dimensional polymers," Nat Chem 2013, 5 (6), 453-465.

Dumcenco, D.; Ovchinnikov, D.; Marinov, K.; Lazić, P.; Gibertini, M.; Marzari, N.; Sanchez, O. L.; Kung, Y.-C.; Krasnozhon, D.; Chen, M.-W.; Bertolazzi, S.; Gillet, P.; Fontcuberta i Morral, A.; Radenovic, A.; Kis, A., "Large-Area Epitaxial Monolayer MoS2," ACS Nano 2015, 9 (4), 4611-4620.

Eda, G.; Yamaguchi, H.; Voiry, D.; Fujita, T., Chen, M.; Chhowalla, M., "Photoluminescence from Chemically Exfoliated MoS2," Nano Letters 2011, 11 (12), 5111-5116.

Falk, D. R. & Aitken, L. P. "Promoting Retention Among American Indian College Students," Journal of American Indian Education 23 (1984), 9 pages.

Fonseca, J. J.; Tongay, S.; Topsakal, M., Chew, A. R.; Lin, A. J.; Ko, C.; Luce, A. V.; Salleo, A.; Wu, J.; Dubon, O. D., "Bandgap Restructuring of the Layered Semiconductor Gallium Telluride in Air," Advanced Materials 2016, 28 (30), 6465-6470.

Green, M. D.; Allen Jr, M. H.; Dennis, J. M.; Cruz, D. S.-d. 1.; Gao, R.; Winey, K. I.; Long, T. E., "Tailoring macromolecular architecture with imidazole functionality: A perspective for controlled polymerization processes," European Polymer Journal 2011, 47 (4), 486-496.

(Continued)

*Primary Examiner* — Alexander R Pagano
(74) *Attorney, Agent, or Firm* — Fish & Richardson P.C.

(57) ABSTRACT

Octaaminonaphthalene and a method of synthesizing octaaminonaphthalene are described. A two-dimensional coordination polymer and a method of synthesizing the two-dimensional coordination polymer are described. The two-dimensional coordination polymer includes ligands including anchorage sites, and metal linkers, each metal linker including a metal and an organic moiety. Each metal linker is coupled to two ligands via the anchorage sites. Synthesizing the two-dimensional coordination polymer includes contacting a first liquid precursor with a second liquid precursor at an interface, reacting the metal linker and the water-soluble ligand to yield a two-dimensional coordination polymer at the interface, and removing the two-dimensional coordination polymer from the interface.

17 Claims, 8 Drawing Sheets

(56) References Cited

OTHER PUBLICATIONS

Green, M. D.; Foster, A. A.; Greco, C. T.; Roy, R.; Lebr, R. M.; Epps, I., Thomas H.; Sullivan, M. O., "Catch and release: photocleavable cationic diblock copolymers as a potential platform for nucleic acid delivery," Polymer Chemistry 2014, 5 (19), 5535-5541.

Green, M. D.; Long, T. E., "Designing Imidazole-Based Ionic Liquids and Ionic Liquid Monomers for Emerging Technologies," Polymer Reviews 2009, 49 (4), 291-314.

Green, M. D.; Salas-de la Cruz, D.; Ye, Y.; Layman, J. M.; Elabd, Y. A.; Winey, K. I.; Long, T. E., "Alkyl-Substituted N-Vinylimidazolium Polymerized Ionic Liquids: Thermal Properties and Ionic Conductivities," Macromolecular Chemistry and Physics 2011, 212 (23), 2522-2528.

Green, M. D.; Schreiner, C.; Long, T. E., "Thermal, Rheological, and Ion-Transport Properties of Phosphonium-Based Ionic Liquids," The Journal of Physical Chemistry A 2011, 115 (47), 13829-13835.

Green, M. D.; Wang, D.; Hemp, S. T.; Choi, J .- H.; Winey, K. I.; Heflin, J. R.; Long, T. E., "Synthesis of imidazolium ABA triblock copolymers for electromechanical transducers," Polymer 2012, 53 (17), 3677-3686.

Kong, W.; Bacaksiz, C.; Chen, B.; Wu, K.; Blei, M.; Fan, X .; Shen, Y.; Sahin, H.; Wright, D.; Narang, D. S.; Tongay, S., Angle resolved vibrational properties of anisotropic transition metal trichalcogenide nanosheets. Nanoscale 2017, 9 (12), 4175-4182.

Kory, M. J.; Wörle, M.; Weber, T.; Payamyar, P.; van de PollStan, W.; Dshemuchadse, J.; Trapp, N.; Schlüter, A. D., "Gram-scale synthesis of two-dimensional polymer crystals and their structure analysis by X-ray diffraction," Nat Chem 2014, 6 (9), 779-784.

Lee, C.; Yan, H.; Brus, L. E.; Heinz, T. F.; Hone, J.; Ryu, S., "Anomalous Lattice Vibrations of Single- and Few-Layer MoS2," ACS Nano 2010, 4 (5), 2695-2700.

Lee, S.; Yang, F.; Suh, J.; Yang, S.; Lee, Y.; Li, G.; Sung Choe, H.; Suslu, A.; Chen, Y.; Ko, C.; Park, J.; Liu, K.; Li, J.; Hippalgaonkar, K.; Urban, J. J.; Tongay, S.; Wu, J., "Anisotropic in-plane thermal conductivity of black phosphorus nanoribbons at temperatures higher than 100 K," Nature Communications 2015, 6, 8573, 7 pages.

Lemaitre, M. G.; Donoghue, E. P.; McCarthy, M. A.; Liu, B.; Tongay, S.; Gila, B.; Kumar, P.; Singh, R. K.; Appleton, B. R.; Rinzler, A. G., "Improved transfer of graphene for gated Schottky-junction, vertical, organic, field-effect transistors," ACS Nano 2012, 6 (10), 9095-102.

Li, X.; Zhu, H., "Two-dimensional MoS2: Properties, preparation, and applications," Journal of Materiomics 2015, 1 (1), 33-44.

Lundt, N.; Maryński, A.; Cherotchenko, E.; Pant, A.; Fan, X.; Tongay, S.; Sęk, G.; Kavokin, A. V.; Höfling, S.; Schneider, C., "Monolayered MoSe 2: a candidate for room temperature polaritonics," 2D Materials 2017, 4 (1), 015006, 8 pages.

Lundvall, F.; Vajeeston, P.; Wragg, D. S.; Dietzel, P. D. C.; Fjellvåg, H., "Two New Series of Coordination Polymers and Evaluation of Their Properties by Density Functional Theory," Crystal Growth & Design 2016, 16 (1), 339-346.

Mahmood, J.; Lee, E. K.; Jung, M.; Shin, D.; Choi, H.-J.; Seo, J.-M.; Jung, S.-M.; Kim, D.; Li, F.; Lah, M. S.; Park, N.; Shin, H.-J., Oh, J. H.; Back, J.-B., "Two-dimensional polyaniline (C3N) from carbonized organic single crystals in solid state," Proceedings of the National Academy of Sciences 2016, 113 (27), 7414-7419.

Mak, K. F.; Lee, C.; Hone, J.; Shan, J.; Heinz, T. F., "Atomically Thin MoS2: A New Direct-Gap Semiconductor," Phys. Rev. Lett. 2010, 105 (13), 136805, 4 pages.

Miao, X. C.; Tongay, S.; Petterson, M. K.; Berke, K.; Rinzler, A. G.; Appleton, B. R.; Hebard, A. F., "High Efficiency Graphene Solar Cells by Chemical Doping," Nano Letters 2012, 12 (6), 2745-2750.

Naik, S.; Bhattacharjya, G.; Talukdar, B.; Patel, B. K., "Chemoselective acylation of amines in aqueous media," European Journal of Organic Chemistry 2004, 2004 (6), 1254-1260.

Novoselov, K. S., Geim, A. K., Morozov, S. V., Jiang, D., Zhang, Y., Dubonos, S. V., Grigorieva, I. V. & Firsov, A. A. "Electric field effect in atomically thin carbon films," Science 306, 666-669, doi:10.1126/science.1102896 (2004).

Novoselov, K. S.; Jiang, D.; Schedin, F.; Booth, T. J.; Khotkevich, V. V., Morozov, S. V.; Geim, A. K., "Two-dimensional atomic crystals," Proc Natl Acad Sci U S A 2005, 102 (30), 10451-3.

Pant, A., Mutlu, Z., Wickramaratne, D., Cai, H., Lake, R. K., Ozkan, C. & Tongay, S. "Fundamentals of lateral and vertical heterojunctions of atomically thin materials," Nanoscale 8, 3870-3887, doi:10. 1039/C5NR08982D (2016).

Pant, A.; Torun, E.; Chen, B.; Bhat, S. S.; Fan, X.; Wu, K.; Wright, D. P.; Peeters, F.; Soignard, E.; Sahin, H.; Tongay, S., "Strong Dichroic Emission in Pseudo One Dimensional Material ZrS3," Nanoscale 2016, 8: 16259-16265.

Pubchem, "Compound Summary: Naphthalene-1,2,3,4,5,6,7,8-octamine," Aug. 12, 2020, 7 pages.

Suslu, A.; Wu, K.; Sahin, H.; Chen, B.; Yang, S.; Cai, H.; Aoki, T.; Horzum, S.; Kang, J.; Peeters, F. M.; Tongay, S., "Unusual dimensionality effects and surface charge density in 2D Mg(OH)2," Scientific Reports 2016, 6, 20525, 7 pages.

Tate, D. S. & Schwartz, C. L. "Increasing the Retention of American Indian Students in Professional Programs in Higher Education," Journal of American Indian Education 33, 1993 (1993).

Tongay, S.; Berke, K.; Lemaitre, M.; Nasrollahi, Z.; Tanner, D. B.; Hebard, A. F.; Appleton, B. R., "Stable hole doping of graphene for low electrical resistance and high optical transparency," Nanotechnology 2011, 22 (42), 425701, 6 pages.

Tongay, S.; Hwang, J.; Tanner, D. B.; Pal, H. K.; Maslov, D.; Hebard, A. F., "Supermetallic conductivity in bromine-intercalated graphite," Physical Review B 2010, 81 (11), 6 pages.

Tongay, S.; Suh, J.; Ataca, C.; Fan, W.; Luce, A.; Kang, J. S.; Liu, J.; Ko, C.; Raghunathanan, R.; Zhou, J.; Ogletree, F.; Li, J. B.; Grossman, J. C.; Wu, J. Q., "Defects activated photoluminescence in two-dimensional semiconductors: interplay between bound, charged, and free excitons," Scientific Reports 2013, 3, 5 pages.

Tongay, S .; Zhou, J.; Ataca, C.; Liu, J.; Kang, J. S.; Matthews, T. S.; You, L.; Li, J. B.; Grossman, J. C.; Wu, J. Q., "Broad-Range Modulation of Light Emission in Two-Dimensional Semiconductors by Molecular Physisorption Gating," Nano Letters 2013, 13 (6), 2831-2836.

Wang, C.; Yang, S.; Cai, H.; Ataca, C.; Chen, H.; Zhang, X.; Xu, J.; Chen, B.; Wu, K.; Zhang, H.; Liu, L.; Li, J.; Grossman, J. C.; Tongay, S.; Liu, Q., "Enhancing light emission efficiency without color change in post-transition metal chalcogenides," Nanoscale 2016, 8 (11), 5820-5825.

Wang, G.; Robert, C.; Suslu, A.; Chen, B.; Yang, S.; Alamdari, S.; Gerber, I. C.; Amand, T.; Marie, X.; Tongay, S.; Urbaszek, B., "Spin-orbit engineering in transition metal dichalcogenide alloy monolayers," Nat Commun 2015, 6, 7 pages.

Wu, K.; Chen, B.; Yang, S.; Wang, G.; Kong, W.; Cai, H.; Aoki, T.; Soignard, E.; Marie, X.; Yano, A.; Suslu, A.; Urbaszek, B.; Tongay, S., "Domain Architectures and Grain Boundaries in Chemical Vapor Deposited Highly Anisotropic ReS2 Monolayer Films," Nano Letters 2016, 16 (9), 5888-5894.

Wu, K.; Torun, E.; Sahin, H.; Chen, B.; Fan, X.; Pant, A.; Parsons Wright, D.; Aoki, T.; Peeters, F. M.; Soignard, E.; Tongay, S., "Unusual lattice vibration characteristics in whiskers of the pseudo-one-dimensional titanium trisulfide TiS3," 2016, 7, 12952, 7 pages.

Yang, S.; Cai, H.; Chen, B.; Ko, C.; Ozcelik, V. O.; Ogletree, D. F.; White, C. E.; Shen, Y.; Tongay, S., "Environmental stability of 2D anisotropic tellurium containing nanomaterials: anisotropic to isotropic transition," Nanoscale 2017, 9 (34), 12288-12294.

\* cited by examiner

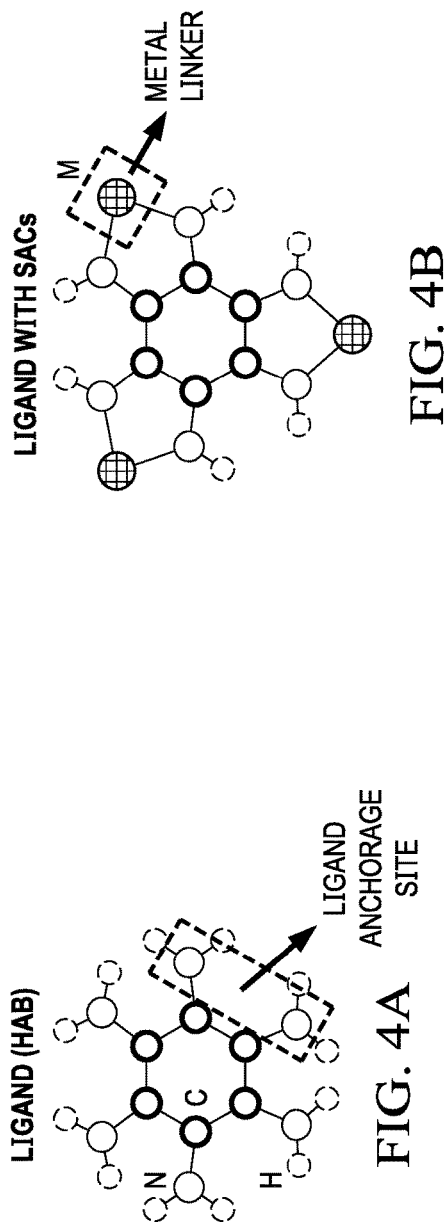
FIG. 4A
FIG. 4B
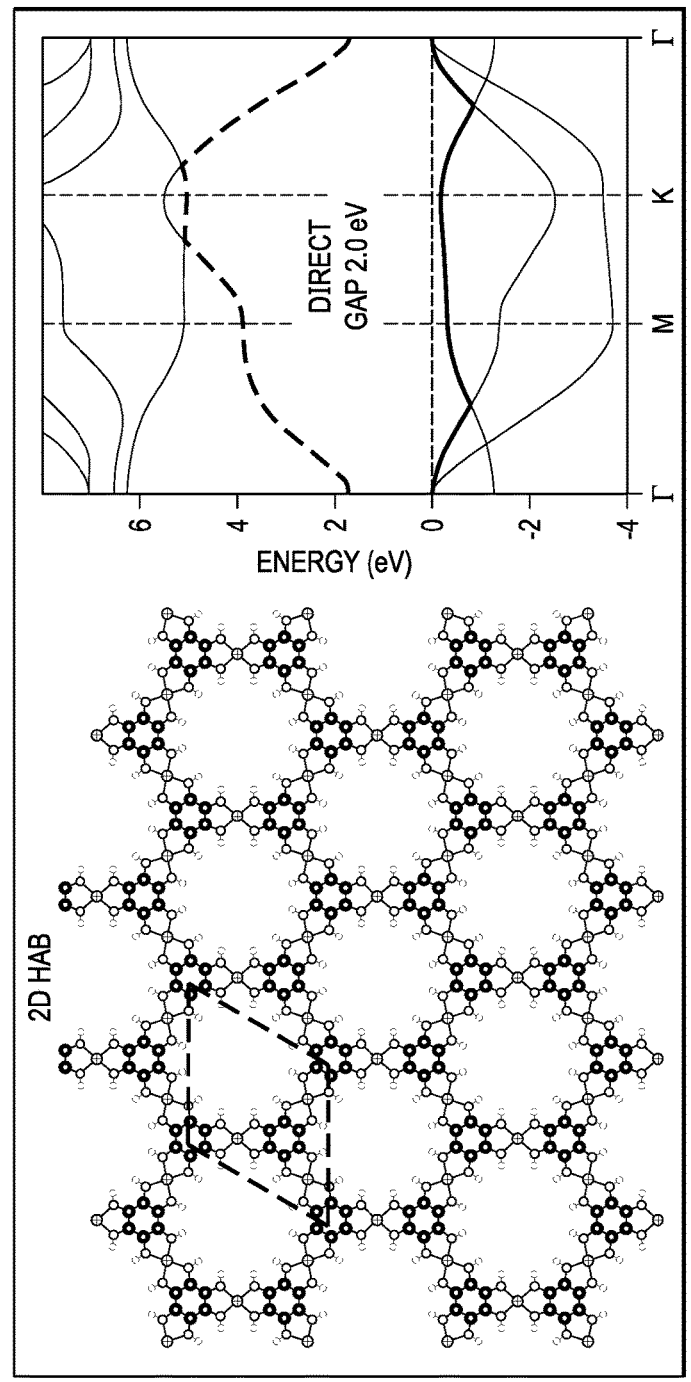
FIG. 5A

TWO-DIMENSIONAL COORDINATION POLYMERS

CROSS-REFERENCE TO RELATED APPLICATIONS

This application is a divisional of U.S. patent application Ser. No. 16/852,288 entitled "TWO-DIMENSIONAL COORDINATION POLYMERS" and filed on Apr. 17, 2020, which claims the benefit of U.S. patent application Ser. No. 62/836,125 entitled "TWO-DIMENSIONAL COORDINATION POLYMERS" and filed on Apr. 19, 2019, which are incorporated herein by reference in their entirety.

TECHNICAL FIELD

This invention relates to two-dimensional coordination polymers.

BACKGROUND

Manufacturing of two-dimensional (2D) polymers onto substrates can be achieved by creating bulk crystals of layered polymers followed by exfoliation or by "bottom up" synthesis methods. These methods typically yield 2D polymers having dimensions far less than 1 cm$^2$, and control of thickness, material crystallinity, and lateral sizes can be difficult to implement. The lack of monomers amenable to 2D polymer synthesis greatly limit the subsequent polymer properties and potential applications.

SUMMARY

A first general aspect includes a compound represented by the following formula:

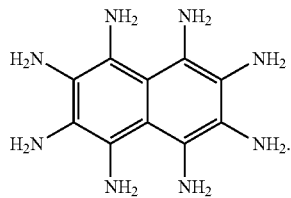 [SMILES: Nc1c(N)c(N)c2c(N)c(N)c(N)c(N)c2c1N]

In a second general aspect, synthesizing the compound of the first general aspect (octaaminonaphthalene) includes reacting 1,36,8-tetranitronaphthalene with sodium methoxide and 4-amino-4H-1,2,4-triazole to yield 2,4,5,7-tetranitronaphthalene-1,3,6,8-tetramine, and reacting 2,4,5,7-tetranitronaphthalene-1,3,6,8-tetramine with phenylhydrazine to yield octaaminonaphthalene.

In a third general aspect, a two-dimensional coordination polymer includes metal linkers and ligands having anchorage sites. Each metal linker includes a metal and an organic moiety, and each metal linker is coupled to two ligands via the anchorage sites.

Implementations of the third general aspect may include one or more of the following features.

The ligand may include hexaaminobenzene or octaaminonaphthalene. The anchorage sites can include N—N, N—O, or both. The organic moiety can be acetylacetonate. The metal is typically Ni, Co, Cu, Zn, Ti, V, Cr, Mn, or Fe. The polymer can be a crystalline polymer with three-fold crystal symmetry.

In a fourth general aspect, synthesizing a two-dimensional coordination polymer includes contacting a first liquid precursor with a second liquid precursor at an interface. The first liquid precursor includes a ligand and the second liquid precursor includes a metal linker. The fourth general aspect further includes reacting the metal linker and the water-soluble ligand to yield a two-dimensional coordination polymer at the interface, and removing the two-dimensional coordination polymer from the interface.

Implementations of the fourth general aspect may include one or more of the following features.

The first liquid precursor is typically an aqueous solution, and the ligand is typically dissolved in the aqueous solution. The ligand includes hexaaminobenzene or octaaminonaphthalene. The first liquid precursor includes an activator selected from the group consisting of sodium carbonate, sodium bromide, sodium chloride, sodium bicarbonate, and sodium hydroxide. The second liquid precursor includes an organic solvent, and the metal linker is dissolved in the organic solvent. The organic solvent may be ethyl acetate. The metal linker can be M(acetylacetonate)$_2$, wherein M is selected from the group consisting of Ni, Co, Cu, Zn, Ti, V, Cr, Mn, and Fe. The polymer is typically a crystalline polymer with three-fold crystal symmetry.

The details of one or more embodiments of the subject matter of this disclosure are set forth in the accompanying drawings and the description. Other features, aspects, and advantages of the subject matter will become apparent from the description, the drawings, and the claims.

BRIEF DESCRIPTION OF THE DRAWINGS

FIG. 4A depicts a top view of a 2D building unit ligand with ligand anchorage sites. FIG. 4B depicts the ligand structure after treatment with metal linker complexes.

FIG. 5A depicts a 2D hexaaminobenzene (HAB) coordination polymer and calculated band structure for ligands with O, N anchorage sites and Co metal linkers.

DETAILED DESCRIPTION

Figure 1C:
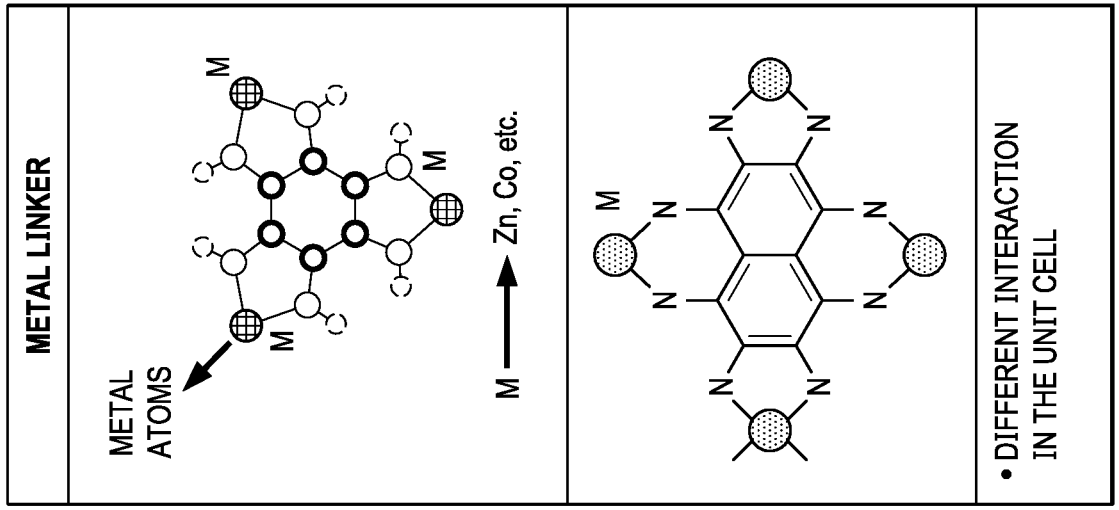
FIG. 1C depicts metal linkers for embodiments of two-dimensional (2D) coordination polymers.
Figure 1B:
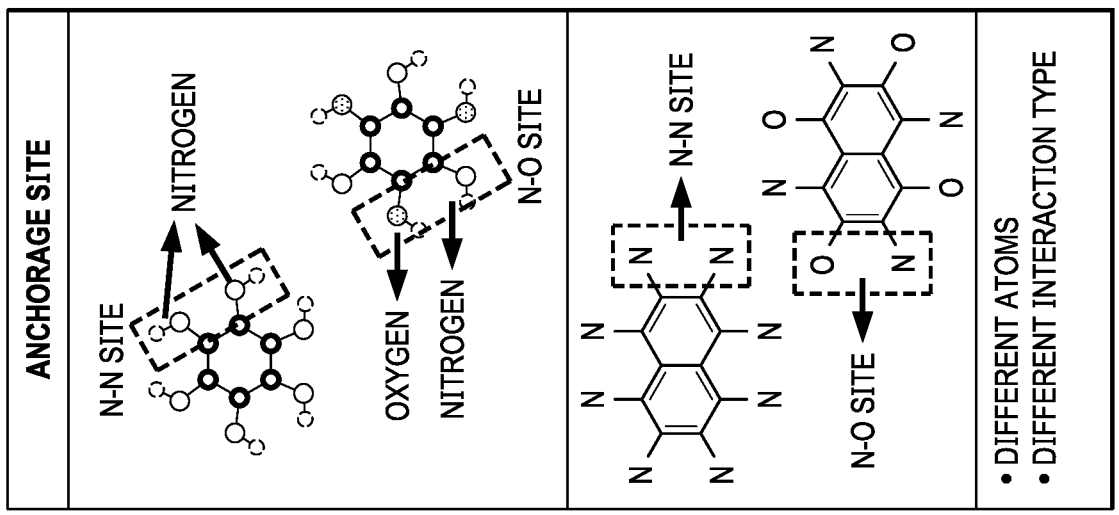
FIG. 1B depicts anchorage sites.
Figure 1A:
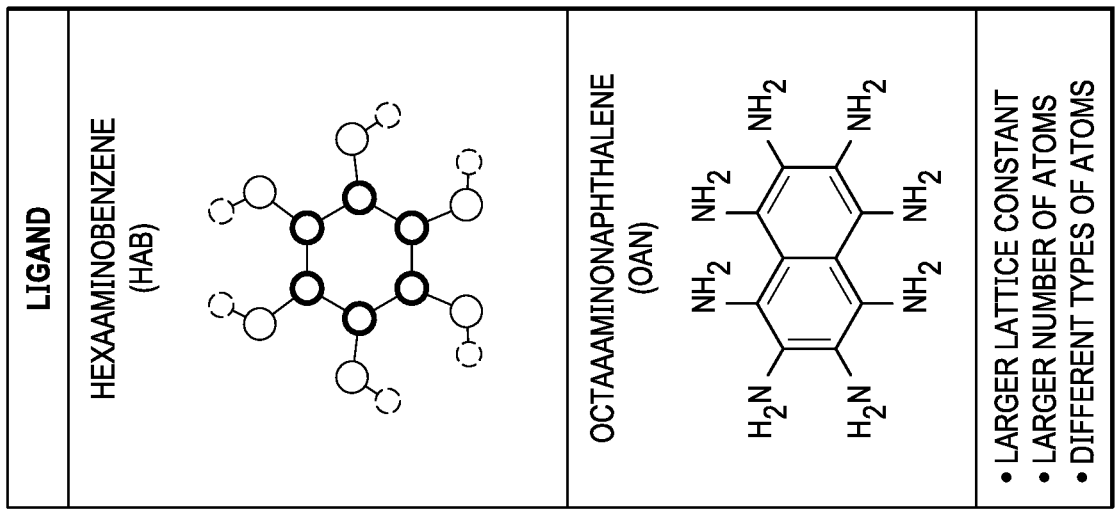
FIG. 1A depicts ligands.

Two-dimensional (2D) coordinate polymers based on hexaaminobenzene (HAB) and octaaminonaphthalene (OAN) ligands are described. As used herein, "two-dimensional polymer" generally refers to a sheet-like monomolecular macromolecule having, consisting of, or consisting essentially of laterally connected repeat units with end groups along all edges. As used herein, "coordination polymer" generally refers to an inorganic or organometallic polymer structure containing metal cation centers linked by organic ligands. FIG. 1A depicts HAB and OAN ligands. FIG. 1B depicts N—N and N—O anchorage sites of HAB and OAN. FIG. 1C depicts metal linkers coupled with HAB and OAN, respectively. Suitable metal linkers include Ni, Co, Cu, Zn, Ti, V, Cr, Mn, Fe, and the like.

Figure 2:
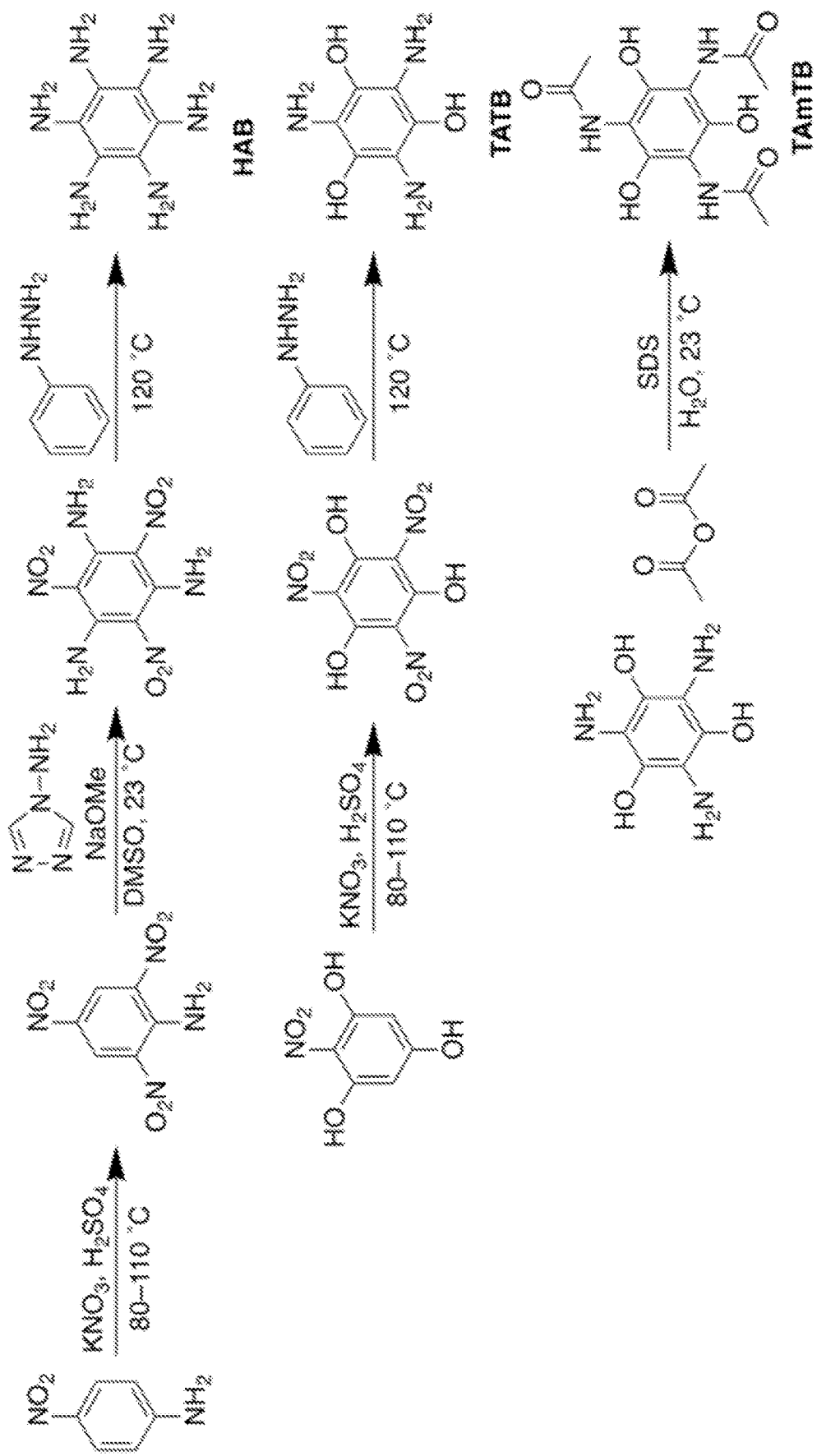
FIG. 2 depicts synthetic schemes to prepare benzene-based monomers with varying anchorage site design (e.g., —OH, —NH$_2$, —NHC(O)CH$_3$).
Figure 3:
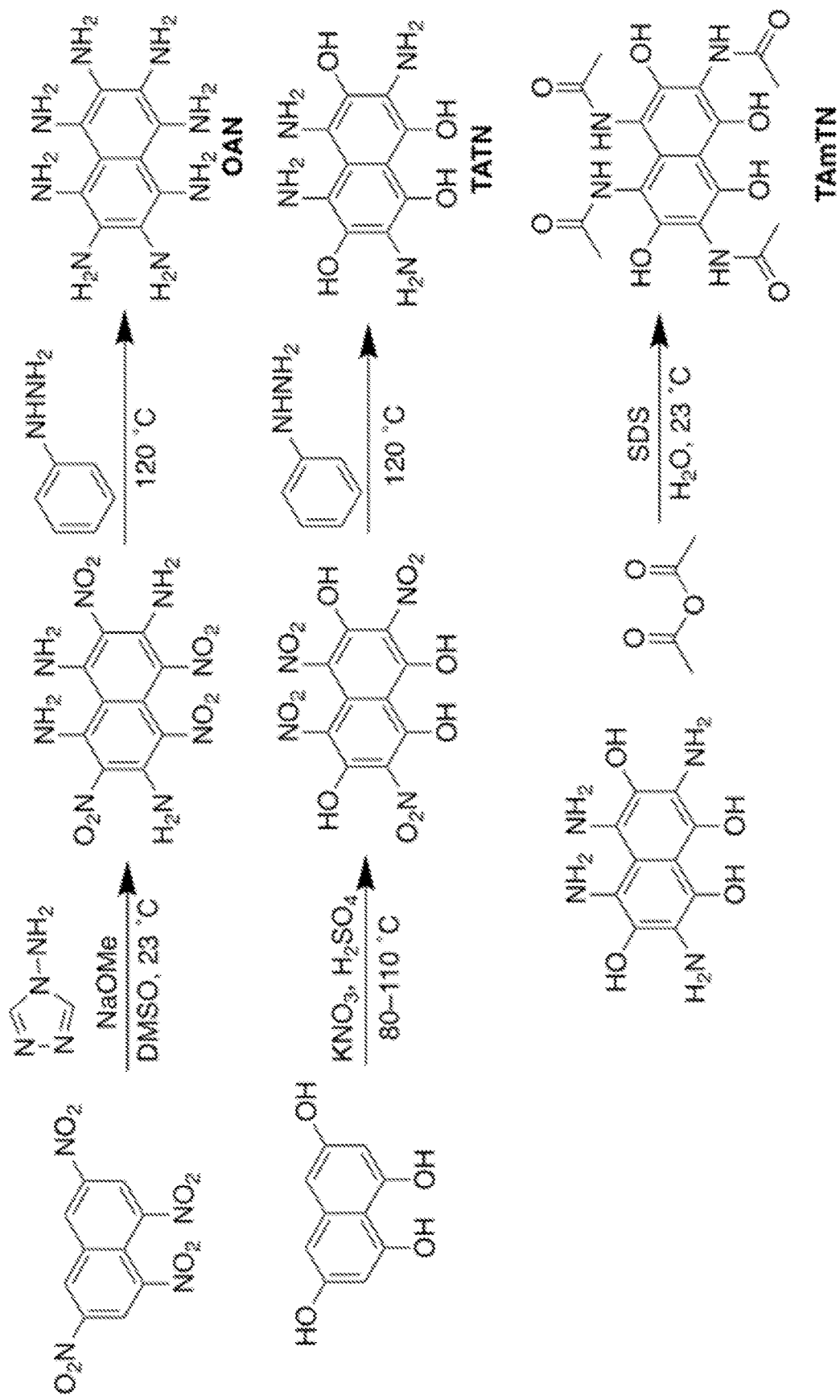
FIG. 3 depicts synthetic schemes to prepare naphthalene-based monomers with varying anchorage site design (e.g., —OH, —NH$_2$, —NHC(O)CH$_3$).

FIG. 2 shows synthetic schemes to prepare monomers based on benzene (HAB-based) with varying anchorage site design (e.g., —OH, —NH$_2$, —NHC(O)CH$_3$). FIG. 3 shows synthetic schemes to prepare monomers based on naphthalene (OAN-based) monomers with varying anchorage site design (e.g., —OH, —NH$_2$, —NHC(O)CH$_3$). OAN is synthesized by amination of 1,3,6,8-tetranitronaphthalene using sodium methoxide and 4-amino-4H-1,2,4-triazole to form 2,4,5,7-tetranitronaphthalene-1,3,6,8-tetraamine. Next, the nitro groups are reduced to amines by phenylhydrazine to form OAN. HAB and OAN provide nitrogen anchorage sites (N—N sites), as shown in FIG. 1B. Triaminotriphenoxybenzene (TAPB) and tetraaminotetraphenoxynaphthalene (TATN) production provide O—N anchorage sites, as shown in FIG. 2.

2D polymers using OAN as a building block are synthesized by adopting a two-phase 2D polymer synthesis route. In this method, the metal-ligand coordination occurs at the liquid-liquid interface formed between two insoluble liquids, each containing a precursor (e.g., HAB or OAN ligands (phase 1) in water), and metal linkers such as M(acac)$_2$ where M=Ni, Co, Cu, etc. (phase 2) in an organic solvent). The reaction yields 2D polymer sheets suspended at the interface, which can be picked up and deposited onto a SiO$_2$/Si substrate for spectroscopy or on a TEM grid for structural characterization.

In one example, a first or monomer phase is prepared by dissolving HAB or OAN monomers in deoxygenated deionized water (10 mM) in inert Ar conditions to prevent oxidization. Then, Na$_2$CO$_3$ (10 mM) and NaBr (2.5 mM) are added to activate the monomer for metal coordination. A second or M(acac)$_2$ phase, where "M" represents a transition metal atom and "acac" represents acetylacetonate, is formed by dissolving ~10 mg of M(acac)$_2$ at a concentration of 120 mM in ethyl acetate (EtOAc). The 2D reaction boundary between these two phases is created by controlled addition of droplets of EtOAc/M(acac)$_2$ onto the aqueous phase. Reaction at the two-phase interface reduces M(acac)$_2$ and binds a single M transition metal atom (from M(acac)$_2$) to two coordination sites on the monomer. This effectively reduces six anchorage sites to three sites, resulting in a 2D coordination polymer with 3-fold crystal symmetry.

As depicted in FIG. 1B, the chemical edge sites of OAN molecule can be engineered to create a 2D polymeric membrane with different chemical structure and physical properties, such as N—N and N—O anchorage sites. To accomplish this, half of the amines in both HAB and OAN are substituted with phenols. First, 2-nitrophloroglucinol is nitrated in a solution of potassium nitrate and sulfuric acid to form 2,4,6-trinitro-1,3,5-triphenoxybenzene. Next, the nitro groups are reduced using phenylhydrazine to form 2,4,6-triamino-1,3,5-triphenoxybenzene (TATB). Similarly, the naphthalene derivative is synthesized from 1,3,6,8-tetraphenoxynapthalene, which is nitrated by a solution of potassium nitrate and sulfuric acid to form 2,4,5,7,-tetraphenoxy-1,3,6,8-tetranitronaphthalene. Finally, this intermediate product is reduced with phenylhydrazine to form 2,4,5,7-tetraamino-1,3,6,8-tetraphenoxynaphthalene (TATN).

For the metal linker, a larger metal orbital (Bohr radius) suggests a higher degree of interaction in the unit cell due to increased orbital overlap between neighboring atomic sites, and the metal atomic mass and Bohr radius influences the unit cell dimensions. The metal salt is typically loaded into the organic solution separate from the organic ligand. This can be accomplished through the use of M(acac)$_2$ salts, which are soluble in toluene and ethyl acetate. Suitable metal linkers include Ti, V, Cr, Mn, Fe, Co, Ni, Cu, and Zn.

Figure 4D:
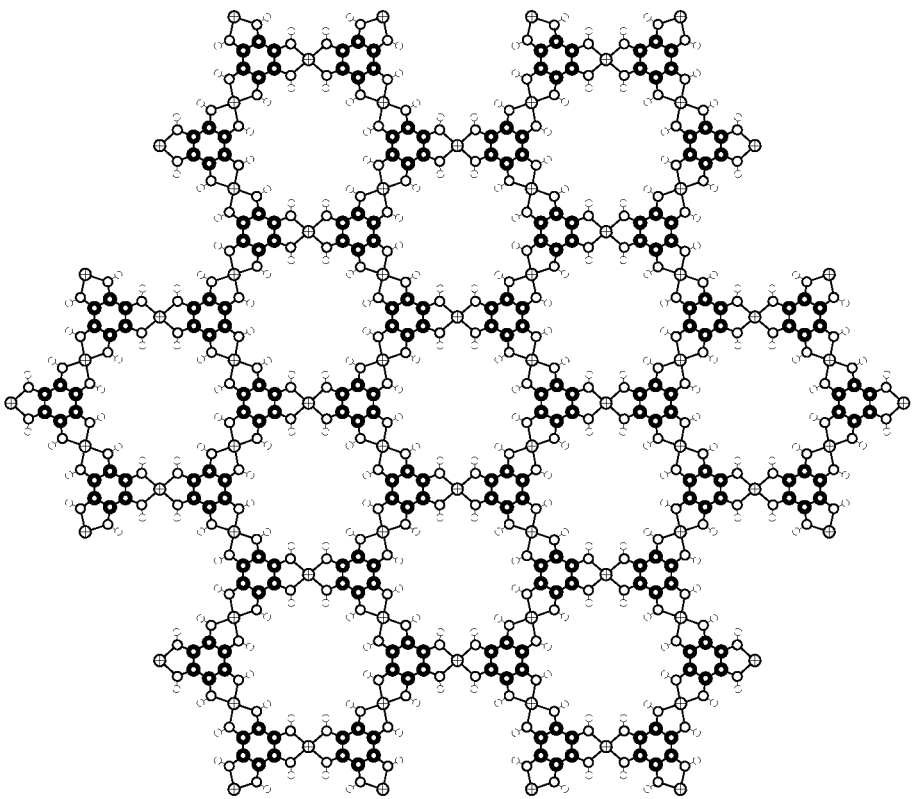
FIGS. 4C and 4D depict a top view of a 2D coordination polymer, with a repeating unit having one ligand and three metal linkers.
Figure 4C:
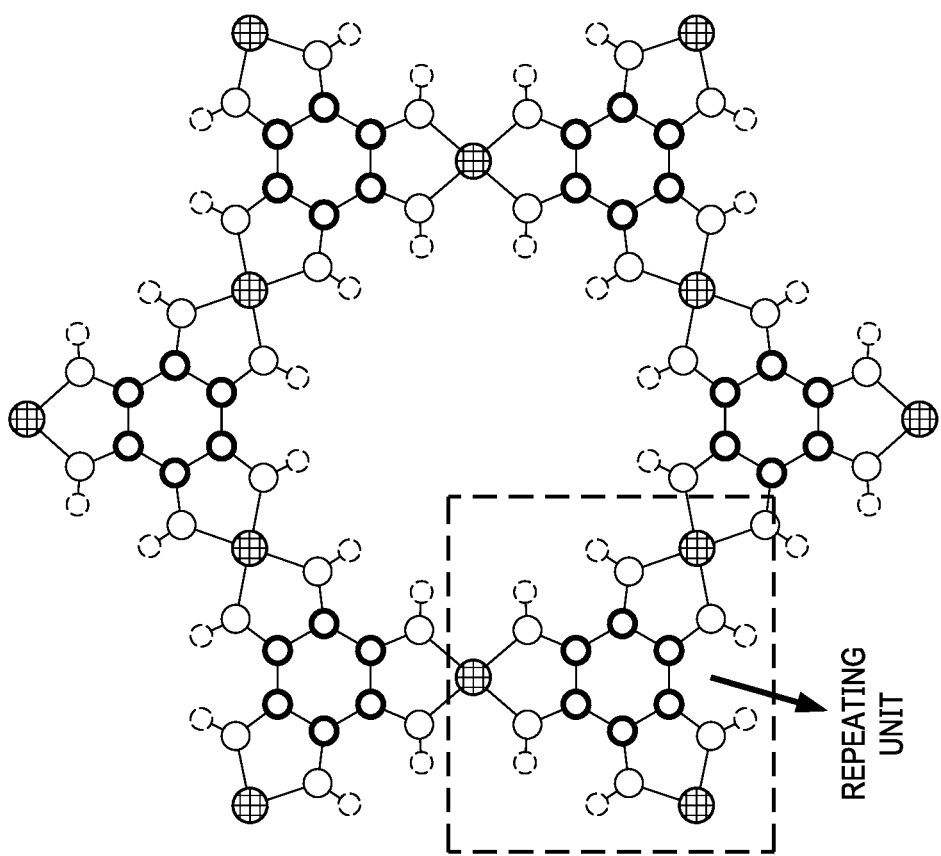

FIG. 4A shows a top view of a 2D building unit HAB ligand. The dashed box indicates the ligand anchorage site where metal atom linkers are located. FIG. 4B shows the ligand structure after treatment with metal acetylacetonate (M(acac)$_2$) complexes. The dashed box indicates the single atom catalyst (SAC) metal linker. FIGS. 4C and 4D depict top views of the 2D coordination polymers, with the dashed box indicating a repeating unit containing one ligand and three metal linkers.

Figure 5B:
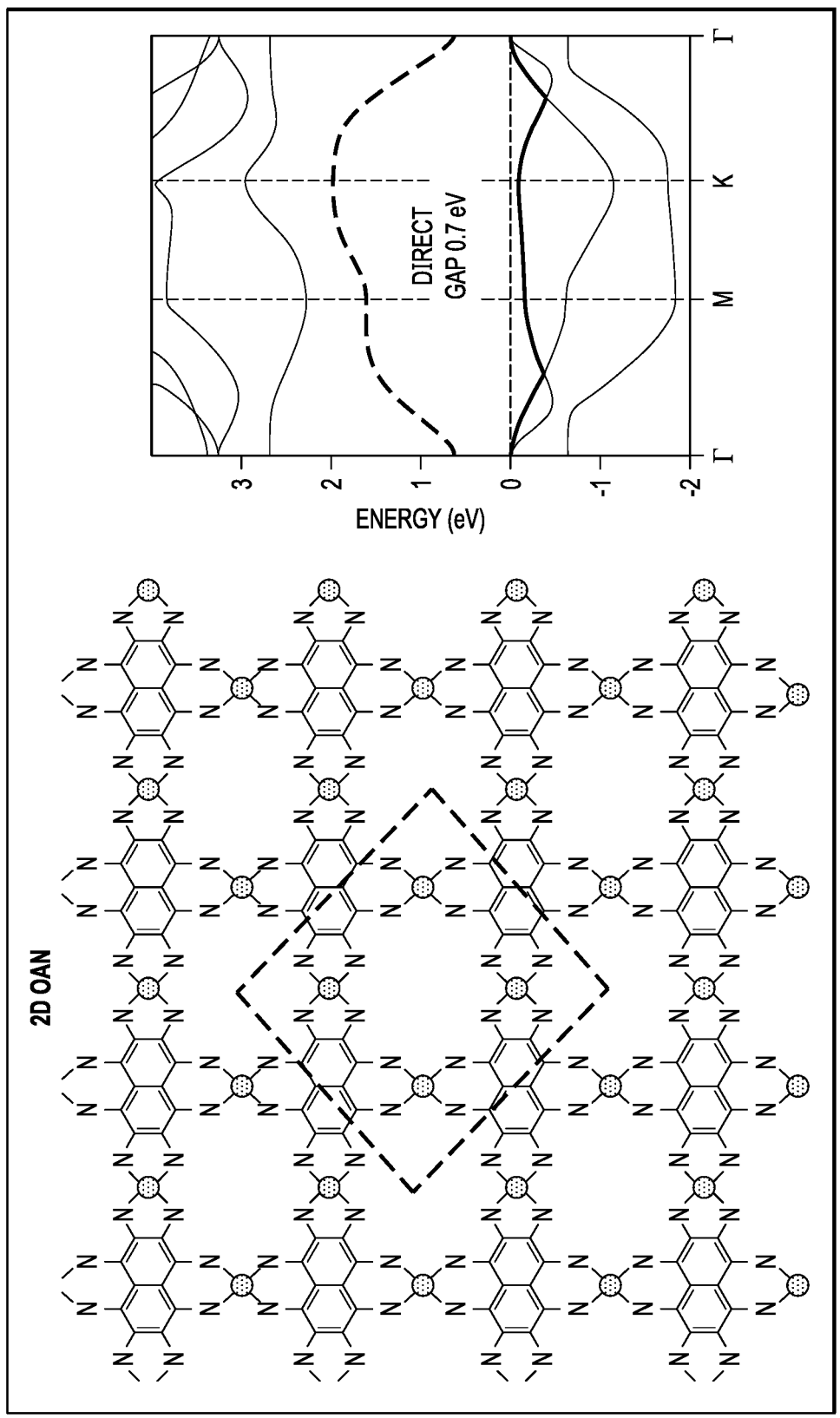
FIG. 5B depicts a 2D octaaminonaphthalene (OAN) coordination polymer and calculated band structure for ligands with O, N anchorage sites and Co metal linkers. The dashed lines indicate unit cells.

FIG. 5A depicts a 2D HAB polymer and a calculated band structure for HAB based ligands with O, N anchorage sites and Co metal linkers. FIG. 5B depicts a 2D OAN polymer and a calculated band structure for OAN based ligands with O, N anchorage sites and Co metal linkers. The dashed boxes indicate unit cells. As seen from the variations in calculated band structures, the band gap (and subsequent impact on material optoelectronic properties) can be varied by altering the monomer structure, ligand composition, and metal.

Figure 6A:
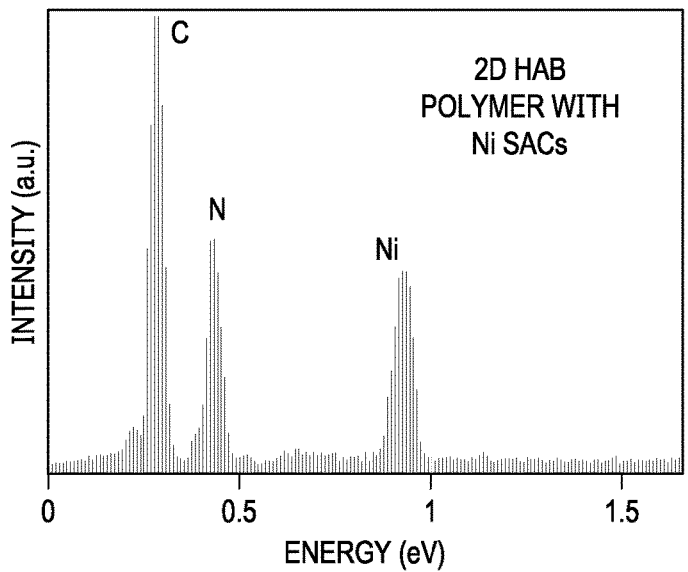
FIG. 6A shows an energy dispersive X-ray (EDS) plot indicating the presence of C, N, and Ni in a 2D HAB polymer.
Figure 6B:
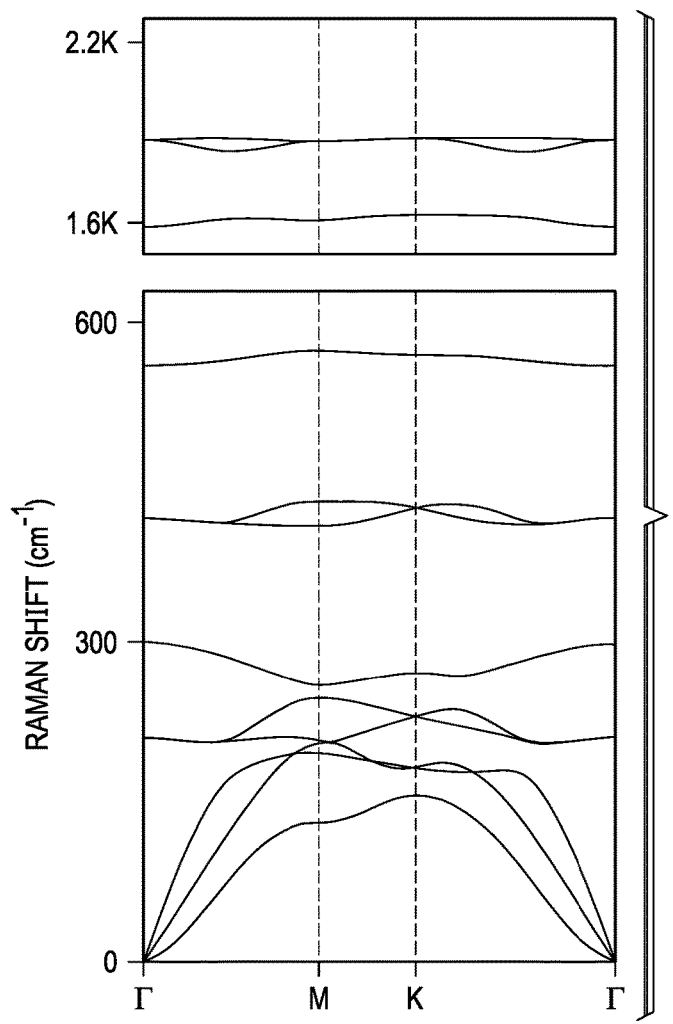
FIG. 6B shows measured and calculated phonon dispersion of a 2D HAB polymer.
Figure 6C:
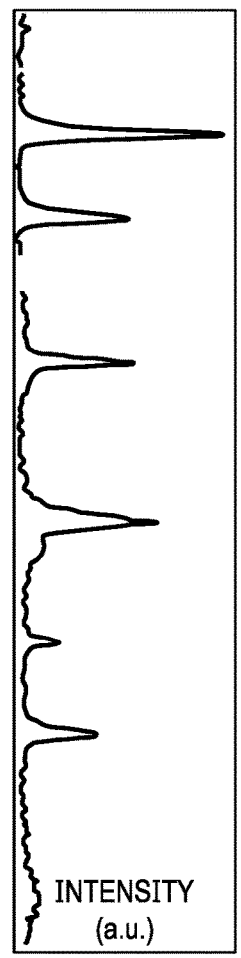
FIG. 6C shows a Raman spectrum of a 2D HAB polymer.

TEM diffraction on 2D HAB polymer with Ni linkers demonstrate the crystallinity of the polymer. SEM images of 2D HAB polymer confirm the layered nature of 2D HAB. AFM images show surface quality, and a line scan plot shows the monolayer nature of 2D HAB. FIG. 6A shows EDS data indicating the presence of C, N, and Ni in 2D HAB. FIG. 6B shows calculated and measured phonon dispersion of 2D HAB. FIG. 6C shows a Raman spectrum of 2D HAB.

Figure 7:
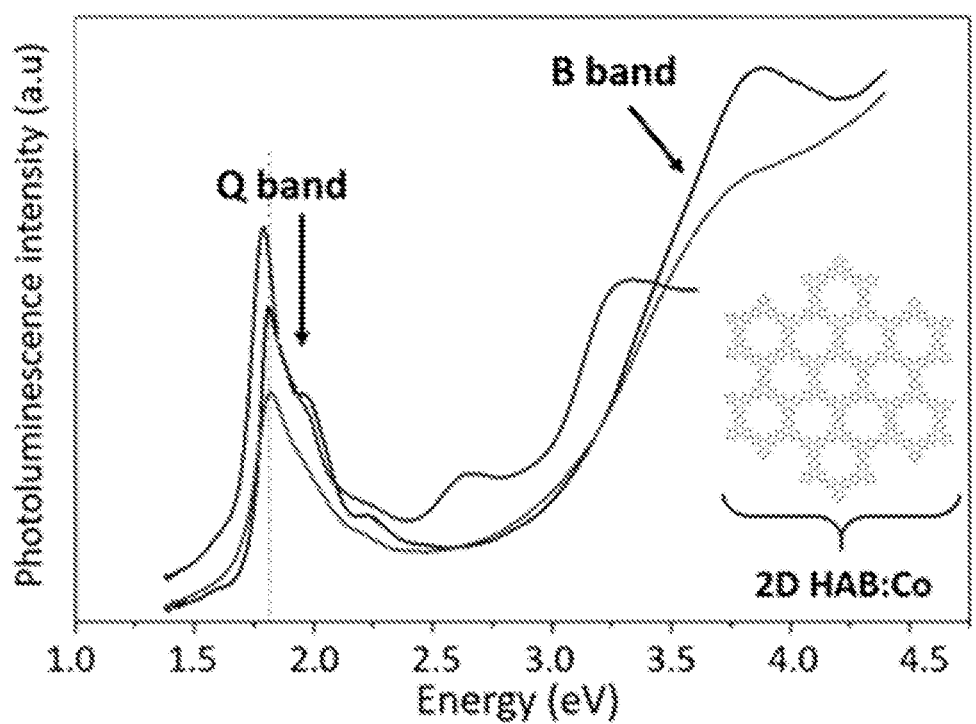
FIG. 7 shows a photoluminescence spectrum of 2D HAB:Co.

FIG. 7 shows typical photoluminescence (PL) spectra acquired from 2D organic HAB:Co sheets. In these graphs, the PL peak position corresponds to the optical band gap of the material, and when measured under the same laser excitation and acquisition conditions, the intensity and FWHM of the PL peak correspond to the light emission (quantum) efficiency and defect concentration, respectively. More specifically, the Q band emission line corresponds to the fundamental band gap of the 2D HAB:Co, whereas the B band marks the $2^{nd}$ highest optical excitation/recombination processes.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A two-dimensional coordination polymer comprising:
   ligands comprising anchorage sites; and
   metal linkers, each metal linker comprising a metal and an organic moiety, wherein each metal linker is coupled to two of the ligands via the anchorage sites,
   wherein the ligands comprise octaaminonaphthalene and the metal comprises Ni, Co, Cu, Zn, Ti, V, Cr, Mn, or Fe.

2. The polymer of claim 1, wherein the polymer is a crystalline polymer with three-fold crystal symmetry.

3. A method of synthesizing a two-dimensional coordination polymer, the method comprising:
   contacting a first liquid precursor with a second liquid precursor at an interface, wherein the first liquid precursor comprises a ligand and the second liquid precursor comprises a metal linker;
   reacting the metal linker and the ligand to yield a two-dimensional coordination polymer at the interface; and
   removing the two-dimensional coordination polymer from the interface,
   wherein the first liquid precursor is an aqueous solution, the ligand is dissolved in the aqueous solution, and the ligand comprises octaaminonaphthalene.

4. The method of claim 3, wherein the first liquid precursor comprises an activator selected from the group consisting of sodium carbonate, sodium bromide, sodium chloride, sodium bicarbonate, and sodium hydroxide.

5. The method of claim 3, wherein the second liquid precursor comprises an organic solvent, and the metal linker is dissolved in the organic solvent.

6. The method of claim 5, wherein the organic solvent comprises ethyl acetate.

7. The method of claim 3, wherein the metal linker comprises M(acetylacetonate)$_2$, wherein M is selected from the group consisting of Ni, Co, Cu, Zn, Ti, V, Cr, Mn, and Fe.

8. The method of claim 3, wherein the polymer is a crystalline polymer with three-fold crystal symmetry.

9. A method of synthesizing a two-dimensional coordination polymer, the method comprising:
   contacting a first liquid precursor with a second liquid precursor at an interface, wherein the first liquid precursor comprises a ligand and the second liquid precursor comprises a metal linker;
   reacting the metal linker and the ligand to yield a two-dimensional coordination polymer at the interface; and
   removing the two-dimensional coordination polymer from the interface,
   wherein the first liquid precursor comprises an activator selected from the group consisting of sodium carbonate, sodium bromide, sodium chloride, sodium bicarbonate, and sodium hydroxide, and the ligand comprises octaaminonaphthalene.

10. The method of claim 9, wherein the second liquid precursor comprises an organic solvent, and the metal linker is dissolved in the organic solvent.

11. The method of claim 10, wherein the organic solvent comprises ethyl acetate.

12. The method of claim 9, wherein the metal linker comprises M (acetylacetonate) 2, wherein M is selected from the group consisting of Ni, Co, Cu, Zn, Ti, V, Cr, Mn, and Fe.

13. The method of claim 9, wherein the polymer is a crystalline polymer with three-fold crystal symmetry.

14. A method of synthesizing a two-dimensional coordination polymer, the method comprising:
   contacting a first liquid precursor with a second liquid precursor at an interface, wherein the first liquid precursor comprises a ligand and the second liquid precursor comprises a metal linker;
   reacting the metal linker and the ligand to yield a two-dimensional coordination polymer at the interface; and
   removing the two-dimensional coordination polymer from the interface,
   wherein the metal linker comprises M(acetylacetonate)$_2$, wherein M is selected from the group consisting of Ni, Co, Cu, Zn, Ti, V, Cr, Mn, and Fe, and the ligand comprises octaaminonaphthalene.

15. The method of claim 14, wherein the second liquid precursor comprises an organic solvent, and the metal linker is dissolved in the organic solvent.

16. The method of claim 15, wherein the organic solvent comprises ethyl acetate.

17. The method of claim 14, wherein the polymer is a crystalline polymer with three-fold crystal symmetry.

\* \* \* \* \*